United States Patent [19]

Stromberg

[11] Patent Number: 5,470,883
[45] Date of Patent: Nov. 28, 1995

[54] METHOD OF TREATING PERIPHERAL VASOCONSTRICTION WITH TAMOXIFEN CITRATE

[76] Inventor: Brent V. Stromberg, 511 Corley Dr., Chesterfield, Mo. 63017

[21] Appl. No.: 247,771

[22] Filed: May 23, 1994

[51] Int. Cl.$^6$ ................................................ A61K 31/135
[52] U.S. Cl. ...................... 514/648; 514/653; 514/654
[58] Field of Search .................................. 514/648, 653, 514/654

[56] References Cited

PUBLICATIONS

NOVADEX (Tamoxifen Citrate) package insert, Zeneca Pharmaceuticals, Wilmington, Del.; Aug. 1993.
Schrijver, J. et al., Investigations on the Nutritional Status of Advanced Breast Cancer Patients. The Influence of Long–Term Treatment with Megestrol Acetate of Tamoxifen; Nutrition and Cancer, vol. 10, No. 4 1987 pp. 231–245.
Lipton, A., The anti–oestrogen tamoxifen is a calcium antagonist in perfused rat mesentery; Cancer Chemotherapy and Pharmacology; (1987) 20:125–127.
Kocsis, J. et al., Effect if the anti–oestrogen Tamoxifen on the development of renal cortical necrosis induced by oestrone+vasopressin administered in rats; Br. J. Exp. Path. (1988), 157–168.
Etgen, A. and Petitti, N., Mediation of Norepinephrine–Simulated Cyclic AMP Acumulation by Adrenergic Receptors in Hypothalmic and Preoptic Area Slices: Effects of Estradiol, Journal of Neurochemistry, vol. 49, No. 6, 1987, pp. 1732–1739.
Baksi, S. et al. Antiestrogen–Induced Alterations of Hypothalmic Dopamine and Norepinephrine Levels in the Female Rat, Neuropharmacology, vol. 20, 1981, pp. 1163–1167.

*Primary Examiner*—Zohreh Fay
*Assistant Examiner*—Phyllis G. Spivack
*Attorney, Agent, or Firm*—Polster, Lieder, Woodruff & Lucchesi

[57] ABSTRACT

A method of modifying peripheral vasoconstriction comprising administering a pharmacologically acceptable dose of tamoxifen.

8 Claims, No Drawings

METHOD OF TREATING PERIPHERAL VASOCONSTRICTION WITH TAMOXIFEN CITRATE

BACKGROUND OF THE INVENTION

This invention relates to a method of blocking or reversing peripheral vasoconstriction, more specifically, to a method of treating peripheral vasoconstriction by the administration of an antiestrogenic agent such as tamoxifen citrate.

It is well known in the practice of medicine that adrenergic agents, notably epinephrine, norepinephrine and dopamine, are potent vasoconstrictors. Extreme caution is used when or if such agents are injected into peripheral tissue such as toes, fingers, ear lobes, the nose or the penis. Due to the profound vasoconstrictive effect of the adrenergic agents, intentional or unintentional injection of an adrenergic agent into peripheral tissue can lead to vasoconstriction, loss of blood flow, and tissue necrosis. In extreme cases, loss of blood flow due to the vasoconstriction may result in amputation of the toe, finger or other body part. It would be advantageous, therefore, to provide a method of blocking or reversing the vasoconstrictive effect of a potent vasoconstrictor by the administration of a readily available, oral, pharmcological agent, such as an antiestrogenic steroid.

It is known that the epinephrine content of the spleen, heart and uterus of rats is increased after the administration of estrogens. Furthermore, it is known that there is an increase in adrenergic nerve terminals and neurotransmitter content in female genital organs caused by estrogen treatment. That sex hormones may play a role in blood flow regulation in the uterus is not unexpected. Furthermore, it has been previously demonstrated, that antiestrogens, such as tamoxifen, have an effect on the development of renal cortical necrosis induced by estrogen plus vasopression. Antiestrogen induced alteration of hypothalmic dopamine and norepinephine levels in rats has also been demonstrated. Moreover, it has been shown that the antiestrogen tamoxifen is a calcium antagonist in perfused rat mesentary. Heretofore, however, no one has taught or suggested the use of an antiestrogen, such as tamoxifen citrate to modify the vasoactive effects of an exogenous adrenergic agent on peripheral blood flow.

SUMMARY OF THE INVENTION

It is a principal object of the present invention, therefore, to provide a method of modifying the effect of vasoconstrictive agents by the use of an antiestrogenic agent.

It is another object of the invention to provide a method of modifying hormonally mediated vasconstriction with an antiestrogenic agent.

Another object of the invention is to provide a method of modifying the effect of vasocontrictive agents on peripheral blood flow by the use of an antiestrogenic agent.

Yet another object of the present invention is to provide a method to modify the effects of peripheral vasoconstrictive agents by the administration of an appropriate salt of tamoxifen.

It is yet another object of the present invention to provide a method of blocking the effect of a peripheral vasoconstrictive agents by the administration of tamoxifen citrate.

It still is another object of the present invention to provide a method of reversing the effect of peripheral vasoconstrictive agents by the administration of tamoxifen citrate.

Yet another object of the present invention is to provide a method of inhibiting or reversing the peripheral vasoconstrictive effect of injectable adrenergic agents such as epinephrine, norepinephrine or dopamine by the oral administration of tamoxifen citrate.

In accordance with the invention, briefly stated, a method of blocking or reversing vasoconstriction, including the peripheral vasoconstrictive effects of an intentionally or an unintentionally administered adrenergic agent such as epinephrine, norepinephrine or dopamine, is provided wherein the subject who receives an injection of such adrenergic agent in a peripheral vascular area is administered a pharmacologically acceptable dose of tamoxifen citrate to inhibit or reverse the peripheral vasoconstrictive effect of the adrenergic agent, restore blood flow, and protect the peripheral tissues.

DESCRIPTION OF THE PREFERRED EMBODIMENT

Tamoxifen citrate (Nolvadex®, Zeneca Pharmaceuticals, Wilmington, Del. 19897) is a trans-isomer of a triphenylethylene derivative. The chemical name is (Z)2-[4-(1,2-diphenyl-1-butenyl)phenoxy]-N, N-dimethylethanamine 2-hydroxy-1,2,3-propranetricarboxylate (1:1). The structure is

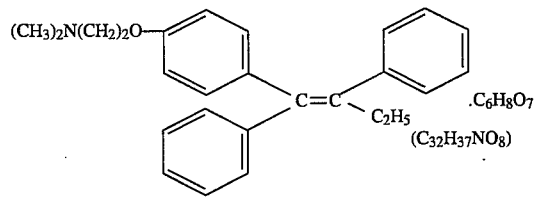

Tamoxifen citrate has a molecular weight of 563.62, the pKa is 8.85, the equilibrium solubility in water at 37 degrees C. is 0.5 mg/mL, and in 0.002N. HCl at 37 degrees C., it is 0.2 mg/mL.

PREVIOUSLY KNOWN CLINCIAL PHARMACOLOGY

Tamoxifen citrate is a nonsteroidal antiestrogen agent which also has estrogen agonist activity. The antiestrogenic effect may be related to its ability to compete with estrogen for binding sites in target tissues such as the breast. Tamoxifen has been shown to inhibit or reverse mammary carcinoma in rats induced by dimethylbenzanthracene (DMBA). Tamoxifen also decreases the frequency of tumor development when administered with DMBA. In humans tamoxifen has been shown to inhibit cell reproduction in estrogen-dependent breast cancer cell cultures. The drug produces no significant effect in tumor cultures without estrogen receptors. There is evidence to suggest that tamoxifen acts within a tumor cell, possibly by blocking estrogen receptors. Other mechanisms of action have been suggested, possibly involving inhibition of messenger RNA by the tamoxifen-estrogen receptor complex within tumor cells. It has been hypothesized that antiestrogen controls the growth of breast cancer by interacting directly in cancer cells with the estrogen receptors rather than antiestrogen binding protein.

Tamoxifen is well-absorbed from the gastrointestinal tract. The drug is metabolised in the liver and only small amounts are excreted in the urine. The distribution half life is 7 to 14 hours; the elimination half-life is greater than 7 days. Preliminary pharmacokinetics in woman using radiolabeled tamoxifen citrate has shown that most of the radioactivity is slowly excreted in the feces with only small amounts appearing in the urine. The drug is excreted mainly as conjugates, with unchanged drug and hydroxylated metabolites accounting for 30% of the total. Blood levels of total radioactivity following single oral does of approximately 0.3 mg/kg reached peak values of 0.06–0.14 micrograms/mL at 4–7 hours after dosing, with 20%–30% of the drug present as tamoxifen. There was an initial half-life of 7–14 hours with secondary peaks four or more days later. The prolongation of blood levels and fecal excretion is believed to be due to enterohepatic circulation.

The primary use of tamoxifen citrate, in the prior art, is in post-surgical adjuvant treatment of early breast cancer in women and treatment of advanced metastatic breast cancer in women and men. Tamoxifen is a first-line agent in the treatment of advanced breast cancer in postmenopausal patients and is alternative to first-line ovarian ablation in premenopausal women. Tamoxifen is also useful in the treatment of anovulatory infertility in women and idiopathic oligospermia in males.

Tumor hormone receptors may help predict which patient will benefit from the adjuvant therapy, but not all breast cancer studies have shown a clear relationship between hormone receptor status and treatment effect. Tamoxifen citrate previously has been shown to be effective in delaying the reoccurence following total mastectomy and axillary dissection or segmental mastectomy, axillary dissection, and breast radiation in woman with axillary node-negative breast cancer. Tamoxifen citrate is effective in delaying reoccurence following total mastectomy and axillary dissection in post-menopausal women with breast cancer.

The normal dose of tamoxifen citrate for the treatment of breast cancer is 10–20 mg twice a day, by mouth. Initial recommended doses are 10 mg twice a day followed by increases to 20 mg twice a day in one month if no response is evident. Higher daily doses (80 mg) have not generally resulted in greater improvement when used to treat breast cancer. The use of higher doses (40 mg) per day of tamoxifen citrate in a woman with metastatic breast cancer to the lung resulted in higher anti-tumor effect. Oral doses of 20 to 40 mg per day and two divided doses are recommended for the treatment of patients with advanced breast cancer and as adjuvant therapy. Increasing the dose to 90 mg daily may produce better response rates in postmenopausal patients with refractory breast cancer. It has shown that dose adjustments are not needed in mild to moderate renal failure.

Reported adverse reactions associated with therapeutic doses of tamoxifen citrate include, but are not limited to, thrombocytopenia, leukopenia, anemia, thromboembolism, arterial thrombosis, mesenteric artery thrombosis, agranulocytosis, lightheadedness, depression, dizziness, headache, lassitude, mental confusion, delusions, hypercalcemia, galactorrhea, nausea, vomiting, pruritus vulvae, vaginal bleeding, endometriosis, priapism, oligospermia, optic disc swelling, retinal hemorrhages, retinopathy, skin rash, flushing, skeletal pain.

Although no cases of tamoxifen citrate overdose have been reported in humans, animals receiving 100 to 200 times the recommended daily dose of developed respiratory difficulties and convulsions. Treatment is systematic and supportive.

NOVEL METHOD OF USE OF TAMOXIFEN CITRATE FOR BLOCKING OR REVERSING THE VASOCONSTRICTIVE EFFECT OF ADRENERGIC AGENTS

The peripheral vasoconstrictive effect of the catecholamine adrenergic agents, notably epinephrine, norepinephrine, and dopamine are well known. Interactions between the catecholamine production and sex hormones have been noted. As stated above the epinephrine content of the spleen, heart, and uterus of rats is increased after administration of estrogens. In addition, there is an increase in adrenergic nerve terminals and neurotransmitter content in female genital organs by estrogen treatment. It is known that sex hormones play a role in blood flow regulation in the uterus. The inventor has determined that sex hormones may interact with or modify the effect of exogenously administered vasoconstrictive agents. Furthermore, the inventor has determined that there is a modification of the effect exogenously administered vasoactive agents by the administration of the estrogen blocking agent, tamoxifen citrate, as shown by the following experimental data and results:

A study utilizing 18 New Zealand adult white rabbits was performed. In the first phase, six rabbits received injections of 0.1 cc. of epinephrine containing solution at a concentration of 1:50,000. This was injected through a 27 gauge needle directly surrounding the central artery of the rabbit ear. Distally peripheral tissue oxygen tension was assessed utilizing a precalibrated transcutaneous oxygen monitor. Measurements were taken prior to injection to maintenance of a steady state. If a steady state was not reached the experiment was discontinued and retried at a later time. Post-injection measurements were taken until the return to baseline levels or up to two hours post-injection. Measurements were taken at five minute intervals preinjection and at three minute intervals post-injection. Control injections utilized 0.1 cc. of intravenous saline solution. In all phases, each animal was used as its own control, both ears being used at different times with one ear receiving the epinephrine and the other receiving the saline control.

In the second phase, six rabbits were used. The animals were pretreated with intravenous injections of estradiol (0.1 mg/kg/day) for two days. Injections of saline control or epinephrine were then randomly given as in phase one and peripheral perfusion as measured by oxygenation was assessed.

In phase three, animals from the second group were treated with estradiol and tamoxifen was added (2.0 mg/kg/day) for two days after allowing three weeks for the original estradiol to wash out. Another group of six animals was pretreated with tamoxifen alone (2.0 mg/kg/day) for two days.

Assessment of peripheral oxygen tension in the rabbit ear artery and its potential modification by saline injection, epinephrine, estradiol, and tamoxifen were evaluated using the transcutaneous oxygen monitor. In no instance did control injections of saline cause any alteration in distal circulation. In addition, it should be noted that the concentration of epinephrine was sufficient to reproduce decreased blood flow to 50% of the preinjection level and cause a return to preinjection levels within 100 to 120 minutes. In no case was there any tissue necrosis associated with this amount of epinephrine.

The results of the study are summarized in Table 1:

TABLE 1

EFFECT OF EPINEPHRINE ON EPINEPHRINE VASOCONSTRICTION

| TIME (MINS.) | SALINE CONTROL n = 5 | TAMOXIFEN n = 6 | ESTROGEN n = 5 | ESTRO + TAMOX. n = 6 | EPINEPHRINE n = 11 |
|---|---|---|---|---|---|
| 0 | 0.968/0.016 | 1.008/0.010 | 0.994/0.043 | | |
| 3 | 1.026/0.027 | 1.005/0.024 | 1.002/0.034 | 1.000/0.037 | 0.986/0.027 |
| 6 | 1.020/0.045 | 0.982/0.017 | 0.988/0.040 | 1.004/0.032 | 1.002/0.011 |
| 9 | 1.001/0.028 | 1.004/0.011 | 0.996/0.033 | 0.987/0.051 | 1.015/0.033 |
| 12 | 0.996/0.017 | 0.989/0.010 | 0.988/0.027 | 0.963/0.059 | 1.016/0.039 |
| 15 | 1.002/0.026 | 1.005/0.006 | 1.022/0.023 | 1.001/0.062 | 1.002/0.033 |
| 18 | 0.988/0.026 | 1.000/0.014 | 0.788/0.052 | 1,040/0.050 | 0.979/0.041 |
| 21 | 1.001/0.015 | 0.999/0.005 | 0.618/0.156 | 1.011/0.062 | 1.001/0.022 |
| 24 | 0.992/0.075 | 1.003/0.014 | 0.524/0.148 | 1.003/0.027 | 1.007/0.035 |
| 27 | 0.932/0.055 | 0.925/0.073 | 0.506/0.143 | 0.990/0.031 | 0.913/0.083 |
| 30 | 0.942/0.079 | 0.930/0.055 | 0.478/0.108 | 0.885/0.166 | 0.707/0.151 |
| 33 | 1.004/0.038 | 0.925/0.045 | 0.048/0.128 | 0.822/0.059 | 0.583/0.143 |
| 36 | 1.036/0.074 | 0.927/0.030 | 0.516/0.095 | 0.915/0.039 | 0.552/0.128 |
| 39 | 1.020/0.078 | 0.935/0.042 | 0,528/0.107 | 0.923/0.656 | 0.485/0.127 |
| 42 | 0.948/0.109 | 0.932/0.060 | 0.061/0.094 | 0.952/0.030 | 0.497/0.119 |
| 45 | 1.012/0.047 | 0.927/0.042 | 0.562/0.177 | 0.998/0.042 | 0.505/0.158 |
| 48 | 0.984/0.060 | 0.945/0.029 | 0.594/0.193 | 0.980/0.057 | 0.489/0.126 |
| 51 | 0.970/0.033 | 0.940/0.032 | 0.546/0.167 | 0.998/0.037 | 0.506/0.151 |
| 54 | 0.986/0.027 | 0.930/0.042 | 0.550/0.209 | 0.995/0.021 | 0.556/0.183 |
| 57 | 1.016/0.048 | 0.947/0.042 | 0.582/0.165 | 0.955/0.061 | 0.574/0.158 |
| 60 | 0.994/0.032 | 0.938/0.037 | 0.618/0.082 | 1.013/0.058 | 0.576/0.175 |
| 63 | 0.980/0.099 | 0.948/0.048 | 0.576/0.193 | 1.020/0.049 | 0.592/0.192 |
| 66 | 1.000/0.023 | 0.927/0.041 | 0.668/0.115 | 1.023/0.051 | 0.605/0.156 |
| 69 | 0.997/0.034 | 0.948/0.041 | 0.716/0/148 | 1.040/0.041 | 0.632/0.188 |
| 72 | | 0.958/0.039 | 0.798/0.158 | 1.009/0.044 | 0.681/0.146 |
| 75 | | 0.970/0.026 | 0.838/0.108 | 1.050/0.014 | 0.704/0.192 |
| 78 | | 0.996/0.009 | 0.834/0.089 | | 0.770/0.099 |
| 81 | | 0.970/0.027 | 0.802/0.104 | | 0.754/0.191 |
| 84 | | 0.980/0.014 | 0.890/0.020 | | 0.801/0.202 |
| | | | | | 0.794/0.165 |
| | | | | | 0.864/0.196 |
| | | | | | 0.846/0.148 |
| | | | | | 0.864/0.131 | data expressed as mean/standard deviation

Pretreatment of animals with estradiol and subsequent injection of epinephrine demonstrated a statistically similar fall in the peripheral blood flow as compared to those animals treated with epinephrine alone. Pretreatment of animals with tamoxifen completely reversed the vasoconstrictive effects of epinephrine. Pretreatment with both estradiol and tamoxifen yielded no further effects over the tamoxifen alone. Thus, the peripheral vasoconstrictive effect of the regional administration of epinephrine into the periarteriolar tissue was completely inhibited by pretreatment with the estrogen blocker, tamoxifen (Nolvadex).

Graph 1. provides another illustration of the aforestated data, with blood flow on the vertical axis compared to time on the horizontal axis.

Although the invention has described the effects of tamoxifen citrate on drug induced peripheral contriction, it will be appreciated by those skilled in the art that the method of the present invention may be used to treat any form of vasoconstriction mediated by sex hormones with an appropriate dose of an appropriate antiestrogenic agent. Therefore, the foregoing description and examples are to be interpreted as illustrative only and should not be construed in a limiting sense.

I claim:

1. A method of modifying the vasoactive effect of epinephrine, norepinephrine or dopamine comprising the administration of a pharmacologically acceptable salt of tamoxifen.

2. The method of claim 1 wherein the tamoxifen salt is administered in a pharmacologically acceptable amount.

3. The method of claim 2 wherein the amount of tamoxifen citrate administered is 2 mg/kg/day.

4. The method of claim 3 wherein said tamoxifen citrate is administered for at least 2 days.

5. A method of modifying the vasoconstrictive effect of an exogenously administered adrenergic agent selected from the group containing epinephrine, norepinephrine, or dopamine comprising the steps of:

injecting the adrenergic agent selected from the group containing epinephrine, norepinephrine, or dopamine into a peripheral vascular area; and administering an oral dose of tamoxifen citrate to modify the vasoconstrictive effect of the administered.

6. The method of claim 5 wherein the tamoxifen citrate is administered in a pharmacologically acceptable amount.

7. The method of claim 6 wherein the tamoxifen citrate is administered in a dosage of approximate 2 mg/kg/day.

8. The method of claim 5 wherein the dosage range is approximately 10 mg to approximately 1000 mg.

* * * * *